United States Patent [19]
Sakuth et al.

[11] Patent Number: 5,849,971
[45] Date of Patent: Dec. 15, 1998

[54] PROCESS FOR CRACKING TERTIARY BUTYL ALCOHOL IN A REACTION DISTILLATION COLUMN

[75] Inventors: Michael Sakuth; Udo Peters, both of Marl, Germany

[73] Assignee: Huels Aktiengesellschaft, Marl, Germany

[21] Appl. No.: 866,013

[22] Filed: May 30, 1997

Related U.S. Application Data

[63] Continuation of Ser. No. 589,542, Jan. 22, 1996, abandoned.

[30] Foreign Application Priority Data

Feb. 11, 1995 [DE] Germany ................. 195 04 556.6

[51] Int. Cl.⁶ .................. C07C 1/20; B01D 3/34
[52] U.S. Cl. ............ 585/639; 585/638; 585/640; 203/29; 203/99; 203/DIG. 6
[58] Field of Search ................ 585/638, 639, 585/640; 203/29, 99, DIG. 6

[56] References Cited

U.S. PATENT DOCUMENTS

| | | | |
|---|---|---|---|
| 4,002,042 | 1/1977 | Pryor et al. | 62/627 |
| 5,231,234 | 7/1993 | Robert P. Arganbright et al. | |
| 5,248,836 | 9/1993 | Bakshi et al. | 568/697 |
| 5,431,888 | 7/1995 | Hickey et al. | 422/191 |
| 5,507,856 | 4/1996 | Rao et al. | 95/45 |

*Primary Examiner*—Elizabeth D. Wood
*Attorney, Agent, or Firm*—Oblon, Spivak, McClelland, Maier & Neustadt, P.C.

[57] ABSTRACT

The present invention is directed to a process for the acid-catalyzed cracking of tertiary butyl alcohol in a reaction distillation column. The advantage of the process of the present invention compared with conventional processes is that the two-phase, liquid-liquid region of the tertiary system TBA/water/isobutene is avoided and a high space-time yield is achieved. This is achieved by the arrangement of the catalyst pack above the liquid phase zone (bottom) and by the use of a dephlegmator thus achieving the isolation of isobutene of high purity.

4 Claims, 1 Drawing Sheet

PROCESS FOR CRACKING TERTIARY BUTYL ALCOHOL IN A REACTION DISTILLATION COLUMN

This application is a Continuation of application Ser. No. 08/589,542, filed on Jan. 22, 1996, now abandoned.

BACKGROUND OF THE INVENTION

1. Field of the Invention

The present invention relates to a process for cracking tertiary butyl alcohol (TBA) over acid ion exchange resin in a reaction distillation column. The process is used for isolating isobutene of high purity with improved economics.

2. Description of the Prior Art

Tertiary butyl alcohol (TBA) is obtained by reaction of isobutene with water. The endothermic cracking of the alcohol, subsequent to the TBA synthesis, is used to isolate isobutene of high purity. The circuitous route via the alcohol is carried out because of the very low boiling point difference or because of the very low separation factor between isobutene and 1-butene, which makes direct distillative fractionation of isobutene containing raffinate streams uneconomical.

The acid-catalyzed cracking (dehydration) of tertiary butyl alcohol (TBA) for isolating isobutene of high purity is a known process. Two different process variants are known here. In one, the cracking is carried out in the liquid phase over acid ion exchange resins, for example in U.S. Pat. No. 4,423,271. In the other, however, the dehydration reaction is carried out in the gas phase over acid aluminosilicate catalysts, for example in JP 184961/86, or over acid aluminum oxides, for example in U.S. Pat. No. 3,665,048. The elimination of water from tertiary butyl alcohol over acid ion exchange resins in the liquid phase is also described in detail in an article by Health et al. ("Acid Resin Catalysis: The dehydration of t-butyl alcohol", AIChe J. 18 (2), 321–326, 1972).

In the first process variant, which is carried out in the liquid phase, note has to be taken of the fact that, in principle, the process can be operated at only small TBA conversions per pass. This is because of the liquid-liquid equilibrium of the ternary system, TBA/water/isobutene which tends to form two phases even at low isobutene concentrations. At high TBA conversions, a TBA-rich organic phase and a relatively low-TBA aqueous phase would form. Owing to the usual hydrophilic properties of the catalyst systems used, the catalyst would preferentially absorb the aqueous phase and the cracking reaction would cease. Higher conversions can be achieved only by the use of high circulating amounts with an intermediate distillative work-up for separating off the isobutene. A further difficulty with this process variant is the amount of isobutene dissolved in the homogeneous liquid phase which is, nevertheless, not so small as to prevent subsequent reactions of this molecular species in the reaction zone. The most important reactions of this type are the acid-catalyzed dimerization and oligomerization. For this reason, $C_8$ and $C_{12}$ components are found in addition to the desired target product isobutene. The undesired $C_8$ molecules are 2,4,4-trimethyl-1-pentene and 2,4,4-trimethyl-2-pentene.

In the second process variant, in which the cracking reaction is carried out in the gas phase, the problems of dimerization or oligomerization of the isobutene formed to give undesired secondary products likewise occur because of the high temperatures and high isobutene concentrations inherent in this process. Attempts are usually made to prevent these reactions by diluting the gaseous starting material stream with inert gas, but this causes additional complication in the work-up.

Both process variants are carried out in conventional (fixed-bed) reactors.

In reaction distillation columns, the arrangement of the catalyst is known both in the liquid phase zone (bottom) of the column and also above the liquid phase zone in the gaseous-liquid region.

EP 0 302 336 B1 describes the cracking of alkyl tertiary-alkyl ethers in a reaction distillation column using an acid cation exchanger ion the liquid phase zone (bottom) of the column as catalyst. In the cracking of methyl tertiary-butyl ether (MTBE) or ethyl tertiary-butyl ether (ETBE), this reaction likewise gives isobutene of high purity. However, owing to the position of the thermodynamic reaction equilibrium, cracking of tertiary butyl alcohol is generally more economical for isolation of isobutene.

SUMMARY OF THE INVENTION

It is therefore an object of the present invention to develop a process for carrying out the cracking of tertiary butyl alcohol in a reaction distillation column to give isobutene of high purity, which makes possible higher TBA conversions per pass than the conventional processes and at the same time has low secondary product formation from isobutene.

This object and other objects as will be better understood from the following descriptions have been obtained by cracking tertiary butyl alcohol in a reaction distillation column, comprising the steps of:

(a) carrying out a reaction over an acid ion exchange resin as catalyst, said catalyst being arranged above a liquid phase zone, (b) partially condensing a top product of said reaction distillation column in a dephlegmator, said dephlegmator being connected to the top of the reaction distillation column, and (c) returning at least a part of a liquid, starting material-rich distillate from said dephlegmator to said top of the column as recycle.

DESCRIPTION OF THE PREFERRED EMBODIMENTS

Figure 1:
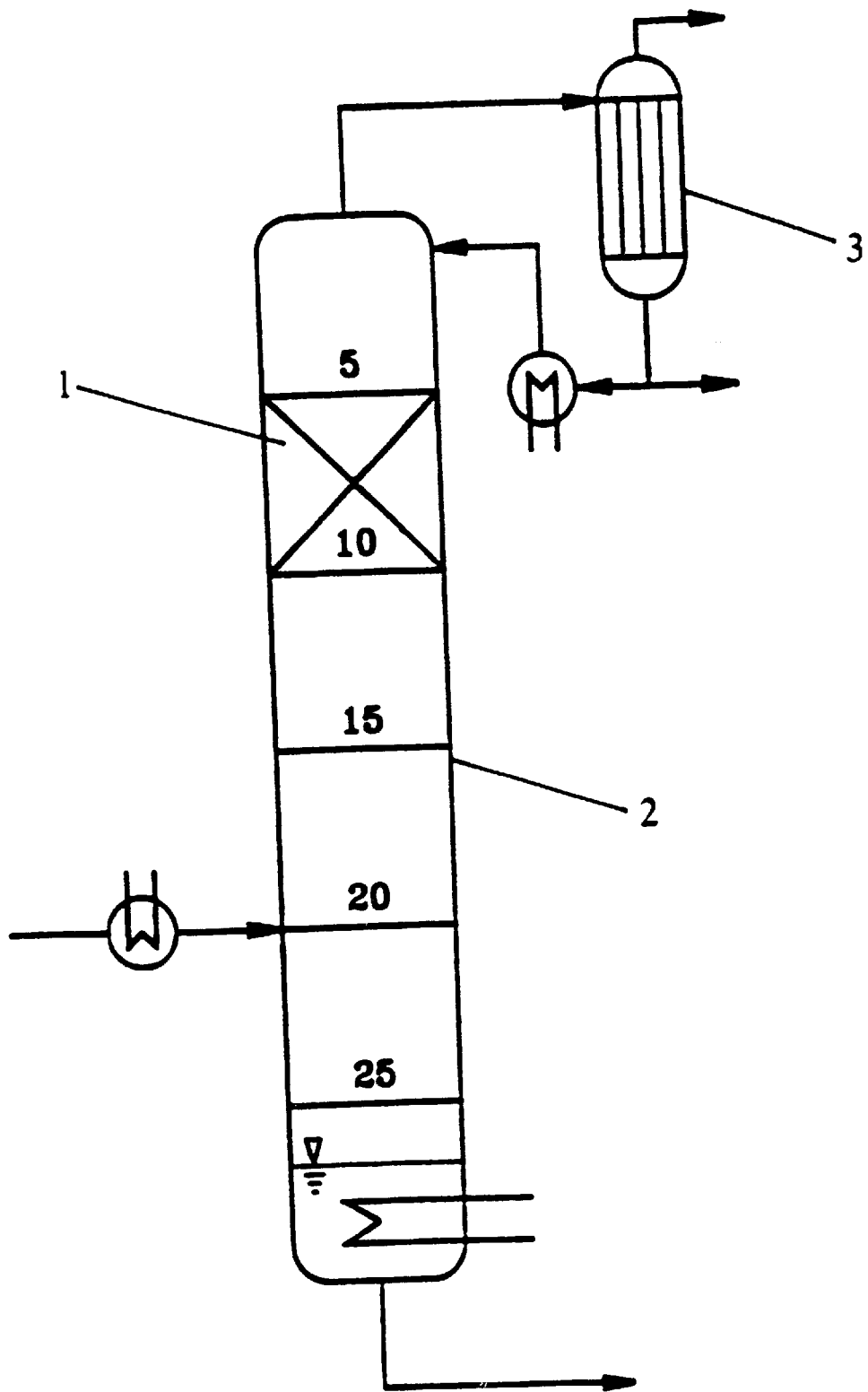
FIG. 1 is a schematic representation of the apparatus which includes a reaction distillation column (2) and a dephlegmator 3.

Referring to FIG. 1, the catalyst 1 used for the cracking of TBA into isobutene and water is an acid ion exchange resin which is arranged, preferably within a distillation pack, above the liquid phase zone (bottom) in the gaseous-liquid region. The reaction product containing at least TBA, isobutene and water is taken off at the top of the reaction distillation column 2 and conveyed to the dephlegmator 3 coupled with the top of the column. By partial condensation, the reaction product is separated in the dephlegmator into a gaseous, isobutene-rich part, which represents the desired process product, and a liquid, starting material-rich part which is returned at least partially as recycle to the top of the column. The use of the dephlegmator at this point serves to overcome the formation of two phases in the liquid-liquid equilibrium of the ternary system TBA/water/isobutene, which would occur in a complete condensation of the reaction product (i.e. the isobutene too). In the liquid phase zone of the column, a water-rich bottom product is taken off. As shown in FIG. 1, the inflow of the at least TBA-rich starting material preferably takes place below the catalyst pack. TBA/water mixtures are usually used as starting material.

Suitable catalysts are strongly acid cation exchange resins, for example those based on styrene-divinylbenzene resins, phenol-formaldehyde resins or coumarone-indene resins, with the aromatic rings bearing sulfonic acid groups. The cation exchange resins are used in their proton-containing form.

A fundamental advantage of the process of the invention is that carrying out the cracking of tertiary butyl alcohol in a reaction distillation column results in a favorable influence on the endothermic equilibrium reaction:

TBA⇌water+isobutene by distillation removal of the reactant isobutene, thus favoring higher TBA conversions.

In a surprisingly advantageous manner, the arrangement according to the invention of the cation exchange pack above the liquid phase zone (bottom) and the coupling of the reaction distillation column with a dephlegmator makes it possible to overcome the formation of two phases in the liquid-liquid equilibrium of the ternary system TBA/water/isobutene. The use of a recycle containing very little isobutene overcomes the otherwise usual decrease in the plate efficiency when two phases are formed. The isobutene content of the recycle is generally less than 5% by weight and the TBA content is more than 80% by weight.

In addition, the recirculation, preferably as completely as possible, of the TBA-rich distillate formed as a liquid in the dephlegmator results in a comparatively high TBA concentration in the reaction section of the column, especially if this is, as preferred, arranged in the vicinity of the top of the column. Furthermore, this also increases the mean residence time of the alcohol in the reaction zone. If in addition, as shown by the preferred embodiment in FIG. 1, the distillation reaction pack is arranged above the inflow in the upper part of the reaction distillation column and a TBA/water mixture of any desired composition is fed into the column, the rectifying section up to the commencement of the reaction zone allows a preliminary separation of the TBA/water mixture as far as the azeotropic point and thus the maximum possible TBA enrichment. This ensures that the mixture reaching the reaction section of the reaction distillation column is always as TBA-rich as possible. Overall, this procedure allows the TBA conversion to be increased so significantly that, in the limiting case of complete recirculation of the liquid distillate, virtually pure isobutene can be taken off at the dephlegmator, while virtually pure water leaves the column in the liquid phase zone (bottom). Usually, TBA conversions of over 70% can be obtained, based on the TBA content of the starting material stream. The isobutene content of the desired product which leaves the dephlegmator in gaseous form is generally above 97% by weight, with the other constituents being (mainly) TBA and water. A preferred distillative work-up of the product for separating off the isobutene is, if required, simple or possible using few separation stages.

Furthermore, the low concentration of isobutene in the liquid phase achieved in the process of the invention largely prevents the formation of undesired secondary products by dimerization or oligomerization of isobutene in the reaction zone. The preferred arrangement of the catalyst pack above the inflow in the vicinity of the top of the column also contributes to this.

In addition, the formation of two phases in the liquid-liquid system TBA/water/isobutene at relatively high isobutene concentrations is overcome by the preferred arrangement according to the invention of the catalyst pack in the upper part of the column or above the inflow and by the use of a dephlegmator at the top of the column. In particular, this enables, without the use of external circuits, a higher space-time yield and also a higher degree of conversion to be achieved. The process of the invention thus allows more economical isolation of isobutene of high purity.

The reaction distillation column is preferably operated in the pressure range from 0.1 to 6.0 $bar_{abs}$ at temperatures up to a maximum of 150° C., preferably up to 130° C. A more preferred operating pressure range of the reaction distillation column is from 2.0 to 4.0 $bar_{abs}$. The particularly preferred operating pressure of the reaction distillation column is about 3.0 $bar_{abs}$. This makes it possible to ensure that the maximum temperature to which the catalyst, the cation exchange resin, is subjected is about 120° C. At this temperature, no significant elimination of sulfonic acid groups from the resin surface is to be expected. The catalyst activity is thus maintained over a prolonged period of time.

Having generally described this invention, a further understanding can be obtained by reference to certain specific examples which are provided herein for purposes of illustration only and are not intended to be limiting unless otherwise specified.

EXAMPLES

Example 1

The cracking of TBA is carried out in a pressure column fitted with bubble cap trays. The column, which is operated adiabatically, has the following dimensions and arrangements:

Internal diameter: 80 mm:
Arrangement:
  a total of 5 sections each having 5 bubble cap trays
  the 2nd-top section is a reaction section, fitted with woven metal pack which is filled with the catalyst (acid cation exchanger). Experimental distillation reaction packs as are described, for example, in U.S. Pat. No. 5,073,236 were used.

The starting material, consisting of 87% by weight of TBA and of 13% by weight of water, is introduced undercooled at a temperature of 90° C. onto tray 20 of the column. The top product is taken off and cooled to about 35° C. in the attached dephlegmator. This temperature and a column pressure of 2.8 $bar_{abs}$ ensures that the isobutene is preferentially in the vapor phase, while the content of TBA and water in this phase is low. A significantly lower temperature would cause appreciable isobutene condensation which would lead to formation of two phase in the liquid-liquid system and thus in the recycle. Thus, a very isobutene-rich vapor phase (97% by weight of isobutene) is taken off from the dephlegmator, which represents the desired product. In addition, part of the distillate is bled from the process. The remainder is heated to about 70° C. and fed to the top of the column.

Table 1 gives an overview of the streams and their composition. The reflux ratio is 1.7.

TABLE 1

STREAMS AND THEIR MAIN CONSTITUENTS (Rounded Off)

|  | kg/h | % by wt. (mol %) TBA | % by wt. (mol %) water | % by wt. (mol %) isobutene |
|---|---|---|---|---|
| Starting material | 2.31 | 87 (62) | 13 (38) | 0 (0) |
| Desired product | 0.72 | 2 (1) | 1 (3) | 97 (96) |
| Distillate taken off | 0.88 | 82 (57) | 13 (38) | 5 (5) |
| Bottom product | 0.71 | 40 (14) | 60 (86) | 0 (0) |

Variation of the reflux ratio allows the TBA conversion to be significantly increased to well above 90%, based on the TBA content in the starting material stream.

Although the present invention has been described with reference to specific details of certain embodiments thereof, it is not intended that such details should be regarded as limitations upon the scope of the invention except insofar as they are included in the accompanying claims.

What is claimed as new and desired to be secured by letters patent of the U.S. is:

1. A process for producing isobutene, comprising the steps of:

(a) cleaving tertiary butyl alcohol in a reaction distillation column in content with an acid ion exchange resin as catalyst, said tertiary butyl alcohol being fed to said reaction distillation column below the catalyst,, said catalyst being arranged above a liquid phase bottom zone, (b) partially condensing a top product of said reaction distillation column in a dephlegmator, said dephlegmator being connected to the top of the reaction distillation column, (c) returning at least a part of a liquid, tertiary butyl alcohol-rich distillate from said dephlegmator to said top of the column as recycle, and (d) recovering isobutene.

2. The process according to claim 1, comprising recirculating substantially all of said liquid tertiary butyl alcohol-rich distillate to said top of said reaction distillation column.

3. The process according to claim 1, further comprising maintaining a pressure in said reaction distillation column between 0.1 and 6.0 $bar_{abs}$ at a temperature of up to 150° C.

4. The process according to claim 3, further comprising maintaining a pressure in said reaction distillation column between 2.0 and 4.0 $bar_{abs}$ at a temperature of up to 130° C.

* * * * *

UNITED STATES PATENT AND TRADEMARK OFFICE
CERTIFICATE OF CORRECTION

PATENT NO. : 5,849,971
DATED : December 15, 1998
INVENTOR(S) : Michael SAKUTH et al.

It is certified that error appears in the above-identified patent and that said Letters Patent is hereby corrected as shown below:

On the title page, item [30], the Foreign Application Priority Data information should read:

--Feb. 11, 1995 [DE] Germany .............................195 04 555.6--

Signed and Sealed this

Twenty-ninth Day of June, 1999

Attest:

Q. TODD DICKINSON

*Attesting Officer*           *Acting Commissioner of Patents and Trademarks*